United States Patent [19]

Michaelis et al.

[11] 4,090,072
[45] May 16, 1978

[54] METHOD FOR DETERMINATION OF ECONOMICALLY INTERESTING METALS IN CONTENT OF MANGANESE NODULES

[75] Inventors: Walfried Michaelis, Seevetal; Agmar Müller, Kroppels-hagen; Hans Ulrich Fanger, Reinbek; Rudolf Pepelnik, Bornsen, all of Germany

[73] Assignee: Gesellschaft fur Kernenergie in Schiffbau u. Schiffahrt mbH, Geesthacht-Tesperhude, Germany

[21] Appl. No.: 700,129

[22] Filed: Jun. 28, 1976

[30] Foreign Application Priority Data

Jul. 5, 1975 Germany .............................. 2530146

[51] Int. Cl.$^2$ .............................................. G01V 5/00
[52] U.S. Cl. .................................... 250/255; 250/253
[58] Field of Search ................................ 250/253, 255

[56] References Cited

U.S. PATENT DOCUMENTS

| | | | |
|---|---|---|---|
| 3,638,020 | 1/1972 | Duffey et al. | 250/253 |
| 3,792,253 | 2/1974 | Wylie et al. | 250/253 X |
| 3,942,003 | 3/1976 | Apenberg et al. | 250/255 |

*Primary Examiner*—Archie R. Borchelt
*Attorney, Agent, or Firm*—Walter Becker

[57] ABSTRACT

Presence of metals such as copper and nickel being economically interesting metals are determined as to existence thereof in the content of manganese nodules according to a method by means of analysis of the activation gamma spectrum of manganese nodule samples after a neutron irradiation thereon. The sample is irradiated with fast neutrons and from the resulting gamma spectrum the ratio of radiation intensities of two main component parts preferably manganese and iron is taken in order to determine the percentage metal content by way of empirically obtained geochemical correlation-data which reproduce the percentage parts of further elements dependent upon proportional ratio of two main elements of the manganese lumps.

9 Claims, 5 Drawing Figures

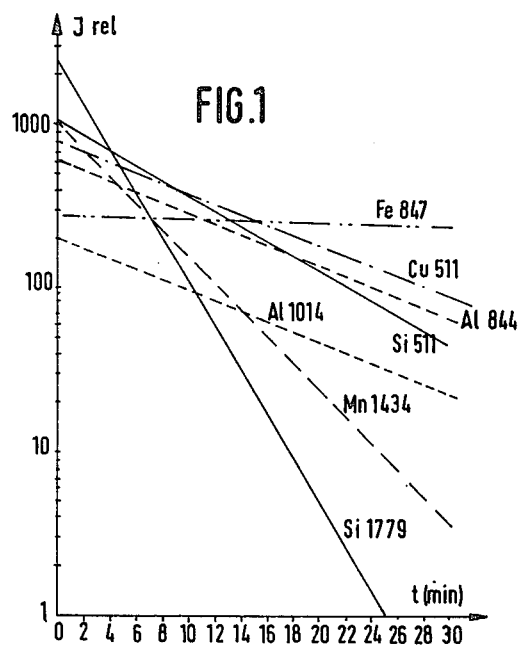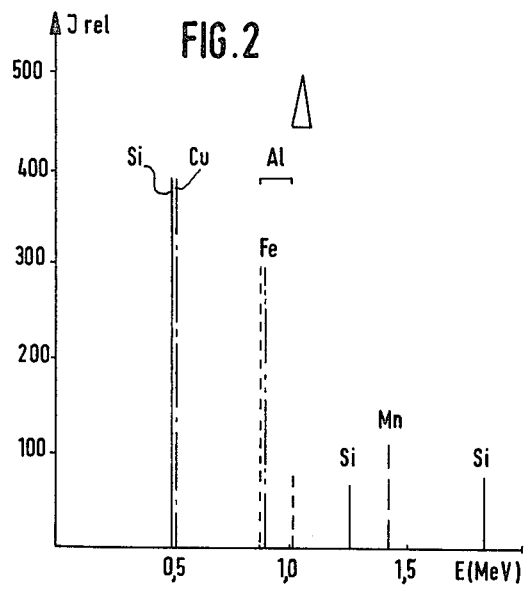

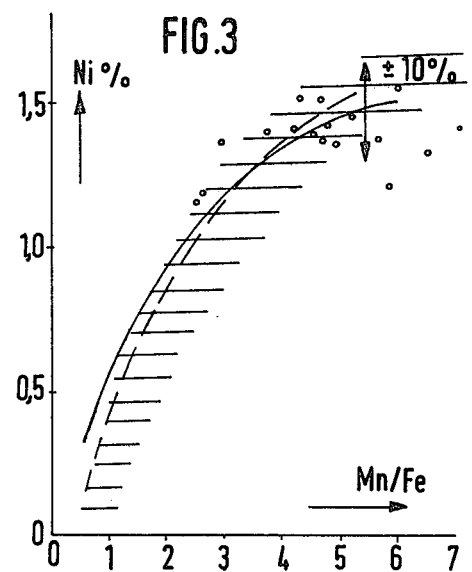
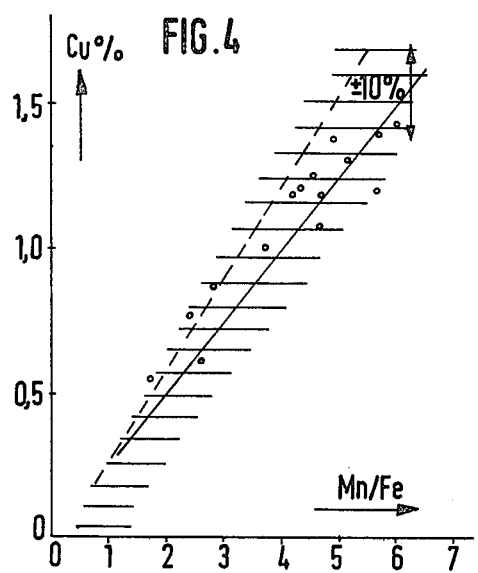

METHOD FOR DETERMINATION OF ECONOMICALLY INTERESTING METALS IN CONTENT OF MANGANESE NODULES

The present invention relates to a method for determination of content of economically interesting metals such as copper and nickel existing in manganese nodules by means of analysis of the activation gamma spectrum of the manganese nodule samples after a neutron radiation.

The exploration of manganese nodule fields in the deep seas requires for valuation of the mining feasibility aside from the determination of other quantities the evaluation of the metal contents in the nodules as to especially economically interesting metals such as copper and nickel. In order to keep the exploration costs as low as possible, there is recommended the integration of in-situ-metal content analyzing device in an encompassing exploration-towing system which then transmits all relevant data in one working step. Also with the preparation and processing of manganese nodules there are necessary element analyses for purposes of process control and regulation. Advantageous for all of these analyses are the so-called nuclear methods which in a known manner utilize penetrating gamma radiation and neutron radiation. They require no or only minimum consumption for sample preparation and average automatically over a greater sample volume a fact which proves advantageous as to the sample being representative.

The utilization of nuclear methods and element analysis of manganese nodules becomes more difficult thereby that conventional methods of activation analysis fail with thermal neutrons. The reason lies in the high manganese content of the nodules, as well as the high capture cross section of the manganese and the advantageous half life of the product nucleus. The induced gamma radiation of the manganese accordingly covers the gamma lines of nearly all other elements. This led to development of the so-called prompt (n, $\gamma$)-method (U. Fanger und R. Pepelnik, Industries Atomiques et Spatiales 4 (1974) 68) for the analysis in-situ during the manganese nodule exploration. The method is in a position to determine substantially all economically interesting metals though thereby there must be taken into consideration certain important disadvantages for practical application: (1) The weight of the entire arrangement is rather high in essence, because of the necessary installation of lead shielding. (2) The structure of the gamma spectrum requires the installation of a high resolution cooled germanium detector. (3) This detector easily shows radiation damage during exposures to fast neutrons. (4) The line intensity is involved in a complicated manner with details of the neutron flux distribution, the nodule composition and the dumping density.

The object of the present invention is to avoid extensively the foregoing disadvantages and to simplify the entire investigation method and to do so in an economically advantageous and price-saving manner.

This object becomes inventively resolved thereby that the sample is irradiated with fast neutrons and then there is taken from the gamma spectrum of the irradiated sample the ratio of the radiation intensities of two main component parts preferably manganese and iron, in order by way of empirically achieved geochemical correlation-data to reproduce the percentage proportion of further elements based on presence of two main elements of the manganese nodules in order to set forth the percentage metal content to be determined. The essential advantage attainable with the invention consists therein that there is possible with the present invention method to determine the absolute contents of the most important metals by way of a simple technical measuring determination of the ratio or relationship of two gamma lines in a spectrum reproduced with relatively few lines. The radioactivity induced by way of irradiation with fast neutrons in the sample material to be investigated either after turning off or removal of the neutron source or after transporting of the sample material to a different measuring location is analyzed with the aid of a gamma detector.

According to a preferred feature of the invention, the penetration of thermal neutrons in the sample chamber radiated with fast neutrons, is reduced with thermal or resonsance absorbers in a ratio of $\phi_{14\,MeV}/\phi_{th} \geq 120$.

This object and other objects and advantages of the present invention will appear more clearly from the following specification in connection with the accompany drawings in which:

FIG. 1 is a diagram concerning the decay behavior of the essential activity resulting by way of 10-minute irradiation of manganese nodules with 14 MeV-neutrons whereby there is set forth as the abscissa the time in minutes and as the ordinate in logarithmic scale the relative intensity of the gamma radiation.

FIG. 2 sets forth idealistically a gamma spectrum gained from the diagram of FIG. 1 after 10 minutes waiting time, whereby the abscissa sets forth the gamma energy in MeV and the ordinate sets forth the relative intensity of gamma radiation.

FIG. 3 represents a geochemical correlation curve for the percentage nickel content dependent upon the Mn/Fe ratio or relationship.

FIG. 4 shows a diagram corresponding to FIG. 3 for the percentage copper content.

Figure 5:
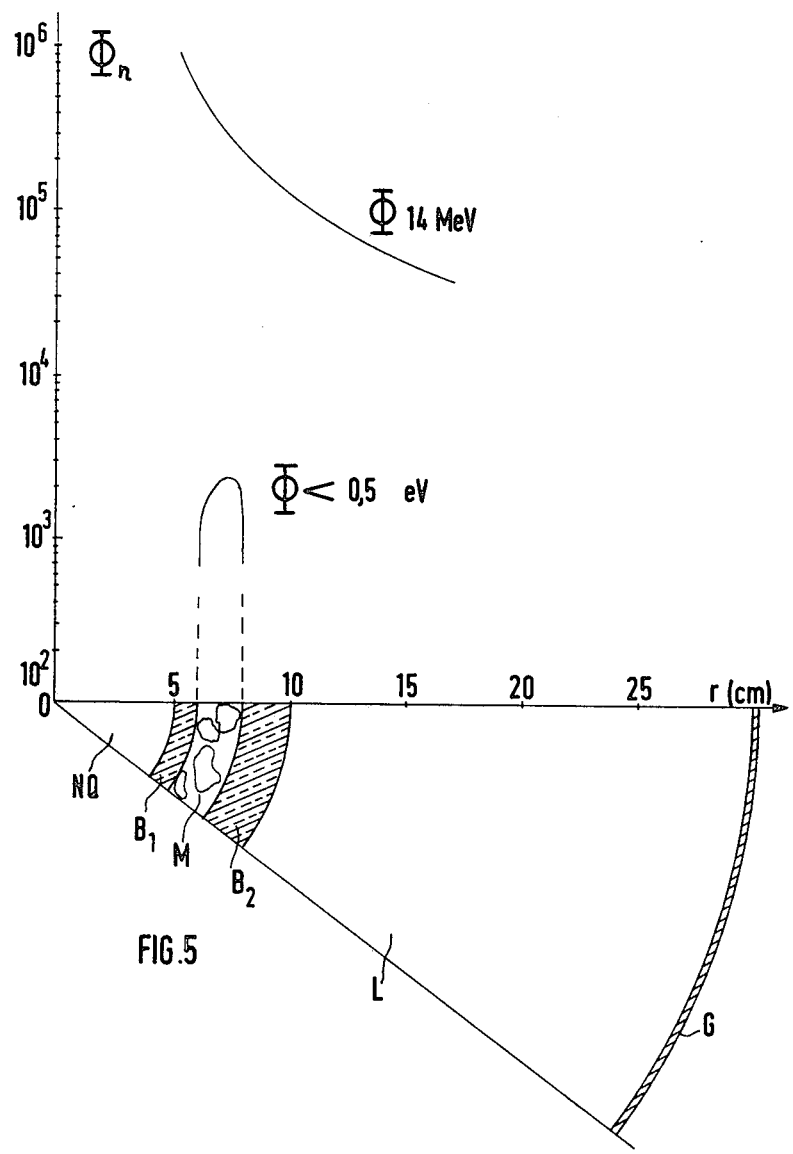
FIG. 5 shows a flux diagram for the fast and thermal neutrons during utilization of an inventive flux depression.

If a sample to be investigated is irradiated with fast neutrons, part of the neutrons leads to (n,p), (n,$\alpha$) or (n,2n) reactions with atomic nucleii which in turn are partly transformed to radioactive nuclides. If the gamma spectrum of these nuclides is analyzed so the individual isotopes are indicated by way of the energy of the observed transitions. The line intensity is related or involved by way of the reaction cross sections, the half-lives, the irradiation time and the waiting time after termination of the radiation with respect to the number of original nucleii for the noted reactions. In the case of manganese nodules, the more intensive gamma lines are produced by the (n,p)- reactions on silicon, aluminum and iron, and the (n,$\alpha$)- reaction on manganese and the (n,2n)- reaction on copper. For a special measuring arrangement and a typical nodule composition, FIG. 1 shows as an example the decay as a function of time of the generated activities with 10-minute radiation time and FIG. 2 represents schematically a gamma spectrum after 10-minute waiting time. There can be recognized therefrom that in this example, the elements iron and manganese can be determined by way of line at 847 respectively 1434 keV whereby the iron line is to be corrected with the aid of the aluminum doublet in a known manner. As shown by the diagram of FIG. 2, the content of copper can also be determined directly other than nickel.

As a source of fast neutrons, there are suitable for this method for example, neutron sealed tubes which deliver neutrons having approximately 14 MeV energy by way of the (d,T)- reaction or natural (radioactive) neutron sources (for instance of a type ($\alpha$,n,), which generate noteworthy portions of fast neutrons (above approximately 6 MeV).

FIGS. 3 and 4 show the variation of the manganese/iron ratio with respect to the absolute contents were nickel and copper. Such correlation were observed by several authors. FIGS. 3 and 4 pertain to concentration correlations of pacific manganese nodules of different locations in a spacing of approximately 80 sm. The dotted fitted curve relates to VALDIVIA-Campaign VA-04 1972.

The cross hatched region was established by Friedrich (Technical University of Aachen) for nodules out of the VALDIVIA-Campaign 05/1973. The full curves in FIGS. 3 and 4 represent a matching to data of 1974 compiled in accordance with the described method for the present invention and based upon locally different locations of the Pacific Ocean with distances of up to 1600 sm. Also, different nodule types were taken into consideration. It is possible accordingly to proceed on the basis that for all economically interesting resources these geochemical correlations are generally valid.

If now inventively there is determined for instance, the nickel concentration and copper concentration subject to utilization of these correlations as described by the foregoing on the basis of the ratio or relationship of two lines pertaining to manganese respectively iron, there is apparent that this method offers and provides the following advantages:

(1) The measurement is reduced to the determination of a peak ratio or relationship. Such relationships can be measured with high accuracy in contrast to absolute intensities.

(2) As apparent from FIG. 2, the gamma spectrum shows a rather simple structure in the method in accordance with the present invention. The energy resolution of a scintillation counter (for instance NaI (Tl); resolution represented in FIG. 2 by way of a triangle) or of a similar simple detector is accordingly sufficient beyond this extent. Such a detector is more robust than a semiconductor counter and requires no cooling.

(3) The characteristics of such a counter in comparison to semiconductor counters show a lesser sensitivity as to the radiation damage by way of fast neutrons.

(4) Since only the ratio or relationship of the concentrations of two elements must be measured, there are eliminated systematic error sources by variation of dumping density, of the nodule composition and of the neutron flux and accordingly of all additional measuring devices. Compared with the (n, $\gamma$)- method representing the previous single nuclear method, there results with the present invention accordingly, an essential instrumental simplification.

(5) If desired, radiation location and measuring location can be separated or the neutron source can be turned off during the measurement. This leads to a reduction of the shielding material and accordingly leads to reduction in the weight of the device or apparatus.

(6) During utilization of sealed neutron tubes or ($\alpha$,n) sources with nominal $\gamma$-emission, there is possible considerable simplification as to the radiation protection problem and handling problems.

(7) The gamma energy range of the measuring spectrum leads to an advantageous detector-response probability. Also, the irradiation geometry and the measuring geometry can be selected at an optimum according to this method. Finally, the analysis is based on the detection of the most predominant elements in the nodules. These advantages permit relative modest neutron source strength.

In order to preclude falsification of the measuring results during utilization of in-situ analyses, there is noted that the activity of $56_{Mn}$ generated in manganese by way of thermal neutron capture cannot be permitted to influence the determination of the manganese/iron ratio or relationship. The thermal neutron flux $\phi_{th}$ must accordingly be suppressed in a suitable manner. One can attain an estimate of the necessary flux depressions, for example, by way of the cross sections for neutron capture in manganese and the (n,p)- reactions on the isotope $56_{Fe}$. Both reactions lead to $56_{Mn}$. The values for the cross sections are 13.3b respectively 110 mb (here for the special case of 14 MeV neutrons). Under these assumptions, there should be accordingly $\phi_{14 MeV}/\phi_{th} \geq 120$, if eventually after application of a suitable correction for neutron capture there should be attained a tolerable error in the analysis. That such flux depressions are attainable in this magnitude is demonstrated for a special case by FIG. 5. With FIG. 5 there is represented in the lower range a radial segment or section of a irradiation arrangement. This irradiation device or apparatus consists for example of a centrally arranged neutron source NQ of 5cm radius. A 1 centimeter thick spherical shell $B_1$ of Boron in the form of $B_4 C$ surrounds this neutron source. A further 2 centimeters thick Boron spherical shell $B_2$ is arranged at a spacing of 8 centimeters from the center of the neutron source. Both of these Boron spherical shells $B_1$ and $B_2$ limit the actual measuring chamber M through which the manganese nodule samples are passed. The actual measuring chamber has a radial thickness of 2cm corresponding to the aforementioned dimensions.

In order to obtain a further suppression of the thermal neutrons and in order to hinder that these are reflected back into the measuring chamber, there is noted that the actual radiation device or apparatus is surrounded with a housing G of which the radius amounts to for example, 30 cm so that between the Boron spherical shell B and the housing G, there results an intermediate space L which can be filled with air or which also can be evacuated. The housing G is surrounded by sea water in operation. The upper curve in FIG. 5 shows the depression of the fast neutron flux dependent upon spacing of the neutron source. The lower curve in the region of the measuring chamber M gives the still remaining thermal neutron flux which means neutrons with energies less than 0.5 eV. There is also recognizable from the ordinate scale that the fast neutron flux is greater by several magnitudes than that of the thermal neutron flux still remaining after the flux depression. The calculation of the neutron flux is based on the assumption of a spherical symmetrical arrangement of the neutron tube (source strength $2 \times 10^8$ n/sec, d = 10 cm). The neutron flux ratio readable from FIG. 5 lies in a maximum at approximately 150.

Further improvements can be attained when for instance, the water between the nodules in measuring volumes is pressed out by way of air or other gases or that the measuring volume is poisoned in the sense of neutron physics with an absorber. In such cases for example, for this special arrangement, the following values are attainable for $\phi_{14 MeV}/\phi_{0.5 eV}$: 370 for $N_2$ (nitrogen) between the nodules 690 for Kr and 14,000 for Hg. A suitable surrounding or hull of the neutron source and the measuring volume with thermal or resonance neutron absorbers and/or the displacement of the water between the manganese nodules and/or the neutron physical poisoning of the measuring volume with absorbing media, permits accordingly a sufficient suppression of the neutron flux.

With the utilization of the method during preparation and processing of manganese nodules, there should be noted that generally these additional measures should be unnecessary because of the lack of water between the nodules and reduced pore-water portion.

It is, of course, to be understood that the present invention is, by no means, limited to the specific showing of the drawings but also comprises any modifications within the scope of the appended claims.

What we claim is:

1. A method for determining the absolute content of economically interesting metals such as copper and nickel in manganese nodules, comprising the following steps:
    (a) irradiating manganese nodule samples with essentially fast neutrons excluding interaction with thermal neutrons;
    (b) recording the activation gamma-ray spectrum;
    (c) taking from the gamma-ray spectrum of the irradiated sample the ratio of radiation intensities of two main components, preferably manganese and iron; and
    (d) determining from this ratio, via empirically obtained geochemical correlational information between the concentration ratio of two main elements and the present fractions of further elements, the absolute percent concentration of metals, not directly disclosed in the spectrum.

2. A method according to claim 1, wherein said irradiating occurs for a duration in a range of minutes.

3. A method according to claim 1, wherein said irradiating and furthermore activation analysis undertaken in situ with a probe towed over the field of exploration.

4. A method according to claim 1, wherein said irradiating occurs in situ in the field of exploration and furthermore analyzing of irradiated samples occurs on board a research vessel within a time of 15 minutes after termination of said irradiating.

5. A method according to claim 1, wherein the penetrating of thermal neutrons into a sample chamber irradiated with fast neutrons is reduced by a factor of $\phi_{14\ MeV}/\phi_{th} \geq 120$ using thermal or resonance absorbers.

6. A method according to claim 1, wherein said irradiating is undertaken in a cylindrical probe chamber means that surrounds the neutron source, and is confined radially inwardly and outwardly with a cylindrical Boron layer.

7. A method according to claim 6, wherein separating between the outer cylindrical Boron layer and outer mantel surrounded with sea water occurs through spacing by way of an annular chamber filled with vacuum, air and the like.

8. A method according to claim 1, wherein there is pressing-out of water between nodule sample particles during neutron irradiating.

9. A method according to claim 1, wherein there is poisoning of intermediate space between the nodule samples with the aid of neutron absorbers.

* * * * *